(12) United States Patent
McEwen et al.

(10) Patent No.: US 9,138,236 B2
(45) Date of Patent: Sep. 22, 2015

(54) TOURNIQUET HAZARD SUPPRESSOR

(75) Inventors: James A. McEwen, Vancouver (CA); Michael Jameson, Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 403 days.

(21) Appl. No.: 13/811,309

(22) PCT Filed: Jul. 4, 2011

(86) PCT No.: PCT/CA2011/000782
§ 371 (c)(1),
(2), (4) Date: Feb. 5, 2013

(87) PCT Pub. No.: WO2012/009787
PCT Pub. Date: Jan. 26, 2012

(65) Prior Publication Data
US 2013/0211445 A1 Aug. 15, 2013

Related U.S. Application Data

(60) Provisional application No. 61/367,079, filed on Jul. 23, 2010.

(51) Int. Cl.
*A61B 17/135* (2006.01)
*A61B 17/00* (2006.01)

(52) U.S. Cl.
CPC ... *A61B 17/1355* (2013.01); *A61B 2017/00123* (2013.01); *A61B 2017/00132* (2013.01); *A61B 2017/00199* (2013.01); *A61B 2017/00212* (2013.01); *A61B 2017/00221* (2013.01)

(58) Field of Classification Search
CPC .............. A61B 17/132; A61B 17/135; A61B 17/1355; A61B 5/02; A61B 5/022; A61B 2017/00119; A61B 2017/00123; A61B 2017/00132; A61B 2017/00199; A61B 2017/00212; A61B 2017/00221; A61F 5/34
USPC .......................................... 606/201, 202, 203
See application file for complete search history.

(56) References Cited

U.S. PATENT DOCUMENTS

| | | | | |
|---|---|---|---|---|
| 4,469,099 | A | * | 9/1984 | McEwen ........................ 606/202 |
| 4,479,494 | A | * | 10/1984 | McEwen ........................ 606/202 |
| 4,635,635 | A | | 1/1987 | Robinette-Lehman |
| 5,607,447 | A | * | 3/1997 | McEwen et al. .............. 606/207 |
| 5,649,954 | A | | 7/1997 | McEwen |
| 5,741,295 | A | | 4/1998 | McEwen |
| 5,855,589 | A | * | 1/1999 | McEwen et al. .............. 606/202 |
| 5,911,735 | A | | 6/1999 | McEwen |
| 5,931,853 | A | * | 8/1999 | McEwen et al. .............. 606/203 |
| 5,968,073 | A | * | 10/1999 | Jacobs .......................... 606/202 |
| 6,051,016 | A | * | 4/2000 | Mesaros et al. .............. 606/202 |
| 6,213,939 | B1 | * | 4/2001 | McEwen ........................ 600/202 |
| 6,475,228 | B1 | * | 11/2002 | Mesaros et al. .............. 606/202 |
| 6,589,268 | B1 | * | 7/2003 | McEwen ........................ 606/202 |

(Continued)

OTHER PUBLICATIONS

European Supplementary Search Report in counterpart EP patent application No. EP 11 80 9101; Apr. 15, 2015; 5 pages.

*Primary Examiner* — Ryan Severson
*Assistant Examiner* — Christian Knauss
(74) *Attorney, Agent, or Firm* — Klarquist Sparkman, LLP

(57) ABSTRACT

A tourniquet hazard suppressor suppresses an action initiated by a user of a surgical tourniquet system having a touchscreen user interface if implementation of that action by the system may be hazardous to a surgical patient.

34 Claims, 3 Drawing Sheets

(56) References Cited

U.S. PATENT DOCUMENTS

| | | | |
|---|---|---|---|
| 6,736,787 B1* | 5/2004 | McEwen et al. | 601/152 |
| 7,048,702 B2* | 5/2006 | Hui | 601/152 |
| 7,166,123 B2* | 1/2007 | Hovanes et al. | 606/202 |
| 8,048,105 B2* | 11/2011 | McEwen et al. | 606/202 |
| 8,425,426 B2* | 4/2013 | McEwen et al. | 600/490 |
| 2002/0016610 A1* | 2/2002 | Hovanes et al. | 606/203 |
| 2003/0236548 A1* | 12/2003 | Hovanes et al. | 606/203 |
| 2004/0147956 A1* | 7/2004 | Hovanes et al. | 606/202 |
| 2006/0253150 A1* | 11/2006 | McEwen et al. | 606/202 |
| 2008/0009680 A1* | 1/2008 | Hassler, Jr. | 600/300 |
| 2008/0262533 A1* | 10/2008 | McEwen et al. | 606/202 |
| 2010/0211096 A1* | 8/2010 | McEwen et al. | 606/203 |

* cited by examiner

US 9,138,236 B2

TOURNIQUET HAZARD SUPPRESSOR

FIELD OF THE INVENTION

This invention relates generally to apparatus for suppressing hazards in surgical tourniquet systems used to establish bloodless fields in surgical patients. The invention relates more particularly, but not by way of limitation, to a hazard suppressor having means to suppress an action initiated by a user of a surgical tourniquet system having a touchscreen user interface if implementation of that action by the system may be hazardous to the surgical patient.

BACKGROUND OF THE INVENTION

Surgical tourniquet systems of the prior art generally include a pneumatic cuff for encircling a patient's limb at a location proximal to the surgical site, a cuff pressure regulator and a tourniquet controller communicating with a user interface. Surgical tourniquet systems are commonly used to facilitate surgery by stopping the flow of arterial blood into a limb for a period of time sufficient for the performance of a surgical procedure, thereby allowing the surgical procedure to be performed in a dry and bloodless surgical field. Published medical literature indicates that every usage of a surgical tourniquet necessarily causes some injury to the nerve, muscle and soft tissue in the limb beneath the cuff and distal to the cuff. To minimize the nature and extent of such injuries, tourniquet users attempt to minimize the level of cuff pressure employed to establish and maintain a bloodless surgical field distal to the cuff. Also to minimize tourniquet-related injuries, tourniquet operators attempt to minimize the duration of tourniquet cuff pressurization.

A basic prior-art system is described by McEwen in U.S. Pat. No. 4,469,099. If the external AC power supply of McEwen '099 is unexpectedly interrupted while the tourniquet cuff is pressurized, an internal battery continues to provide power to the LED displays and audio alarm but the pressure regulator ceases operation and pneumatic valves in the instrument seal off the pressurized cuff to retain the pressure in the cuff for as long as possible or until external AC power is restored and normal operation can resume. Thus in the event of an interruption of external AC power during use in surgery, McEwen '099 prevents hazards for the patient such as the unanticipated flow of arterial blood into the surgical field during a procedure, the loss of large amounts of blood, and in some cases the loss of intravenous anesthetic agent retained in the limb distal to the cuff.

In U.S. Pat. Nos. 6,213,939 and 6,589,268 McEwen describes apparatus for alerting a user and preventing a hazard arising from the use of prior-art surgical tourniquet systems in which a user could erroneously turn off an electrical power switch of a tourniquet instrument without first deflating the tourniquet cuff. In U.S. Pat. No. 5,855,589 McEwen and Jameson describe additional safety apparatus that helps prevent a hazard in dual-cuff tourniquet systems useful for intravenous regional anesthesia.

Despite many such improvements in the prior art, user errors and malfunctions of tourniquet systems can still be hazardous for patients, especially as design complexity increases and as user interfaces improve. As an example of increasing design complexity, tourniquet apparatus of the prior art described by McEwen and Jameson in U.S. Pat. App. No. 20080262533 is responsive to input signals from remote physiologic monitors tracking a range of physiologic changes of the surgical patient, and can adapt tourniquet cuff pressure in response to a patient's changing limb occlusion pressure. Tourniquet apparatus recently described by McEwen et al. in U.S. patent application Ser. No. 12/389,029 allows a user to test the safety and integrity of tourniquet cuffs prior to use, and further allows the user to increase the cuff pressure beyond a normal maximum safety limit if required to meet the specific needs of a specific patient and surgical procedure. Tourniquet apparatus having wireless sensors and remote user interfaces have also been described in the prior art.

The tourniquet apparatus described by McEwen and Jameson in U.S. Pat. No. 5,607,447 employs a user interface that combines a graphical display and a discrete selector switch for improved display of information and for more intuitive selection and input of actions desired by the user. Replacing this prior-art combination of a discrete selector switch and graphical display with a touchscreen user interface may further improve the display of information and the intuitive selection and input of desired actions. However, employing a touchscreen user interface in a surgical tourniquet system may also be associated with additional hazards arising from user errors and malfunctions.

The present invention suppresses an action initiated by a user of a surgical tourniquet system having a touchscreen user interface if implementation of that action by the system may be hazardous to the surgical patient.

DETAILED DESCRIPTION OF THE PREFERRED EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 1:
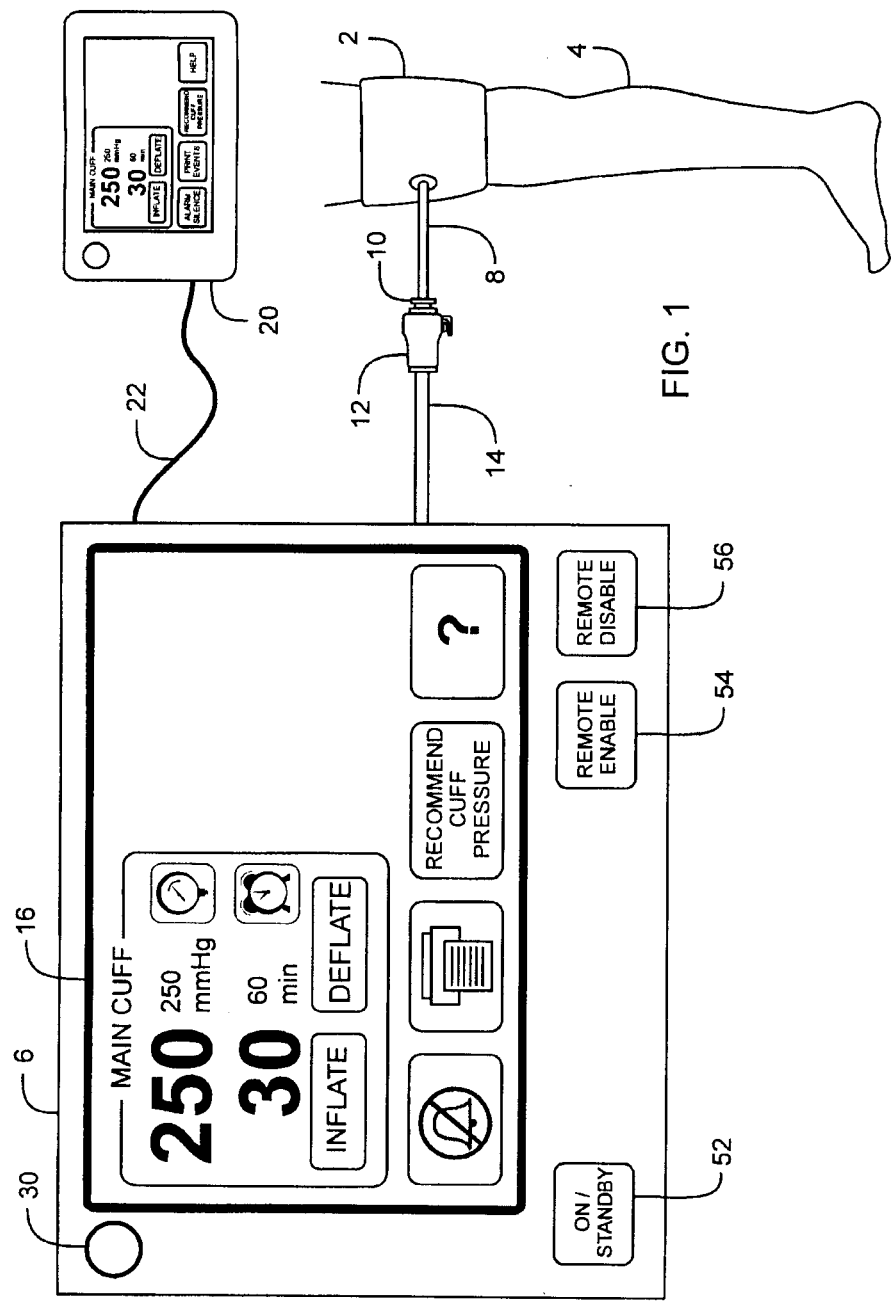
FIG. 1 is a pictorial view of the preferred embodiment in clinical use.

FIG. 1 depicts the tourniquet system of the preferred embodiment in clinical use. Tourniquet cuff 2 is shown applied to a patient limb 4 and pneumatically connected to instrument 6. To stop the flow of arterial blood in limb 4 past cuff 2 during the time a surgical procedure is performed, cuff 2 is supplied with pressurized gas from instrument 6. In the preferred embodiment the gas is air, but it will be apparent that other gases or fluids may be used to pressurize cuff 2. A pneumatic passageway between instrument 6 and cuff 2 is provided by cuff port 8, locking connectors 10 and 12, and tubing 14. Cuff port 8 is fitted with a male locking connector 10, and mates to form a releasable pneumatic connection with female locking connector 12. Female locking connector 12 is fitted to flexible plastic tubing 14 which connects to instrument 6.

Cuff 2 is generally similar in design and construction to the cuffs described by McEwen in U.S. Pat. Nos. 5,741,295, 5,649,954, and by Robinette-Lehman in U.S. Pat. No. 4,635, 635.

To permit a user to control the pressure of gas supplied to cuff 2 by instrument 6, instrument 6 includes a touchscreen user interface 16, as shown in FIG. 1. A user of the preferred embodiment may initiate or confirm desired actions to be performed by instrument 6 by touching the touchscreen within the perimeter of a touchscreen key representative of an action to be performed by instrument 6. For example a user may: initiate the inflation of cuff 2 to a selected reference pressure level; initiate the depressurization of cuff 2 to a pressure level near zero (deflation); set the level of pressure to be maintained in cuff 2 (reference pressure level); set a time limit for an inflation time alarm; temporarily silence audible alarms; and set other operational parameters of instrument 6.

Touchscreen user interface 16 also presents information pertaining to the operation of instrument 6 to the user. Touchscreen user interface 16 may selectively display any of the following information: the level of pressure within cuff 2 as measured by instrument 6 (cuff pressure); the pressure level to be maintained in cuff 2 when cuff 2 is pressurized (reference pressure level); the length of time that cuff 2 has been pressurized (inflation time); pressure warning indicators; alarm reference "limits" or values; alarm messages describing detected alarm events; and other information and instructions pertinent to the operation of instrument 6. To facilitate a clear and rapid understanding of the information presented to the user of instrument 6, alphanumeric text, graphic icons, and color may all be used to convey information.

Inadvertent or unintentional changes in cuff pressure may be hazardous to the patient. For example, an inadvertent reduction in cuff pressure at a time when a surgical procedure is being performed may result in arterial blood flow past cuff 2, loss of blood and delay of surgery due to blood in the surgical field; conversely, an unintended increase in pressure may result in damage to the nerves and soft tissues underlying cuff 2. To help prevent inadvertent and unintentional changes in cuff pressure from occurring in the event of a malfunction of touchscreen user interface 16 or user input errors, the preferred embodiment includes a hazard suppressor 18 as shown in FIGS. 2 and 3 and described below.

Figure 2:
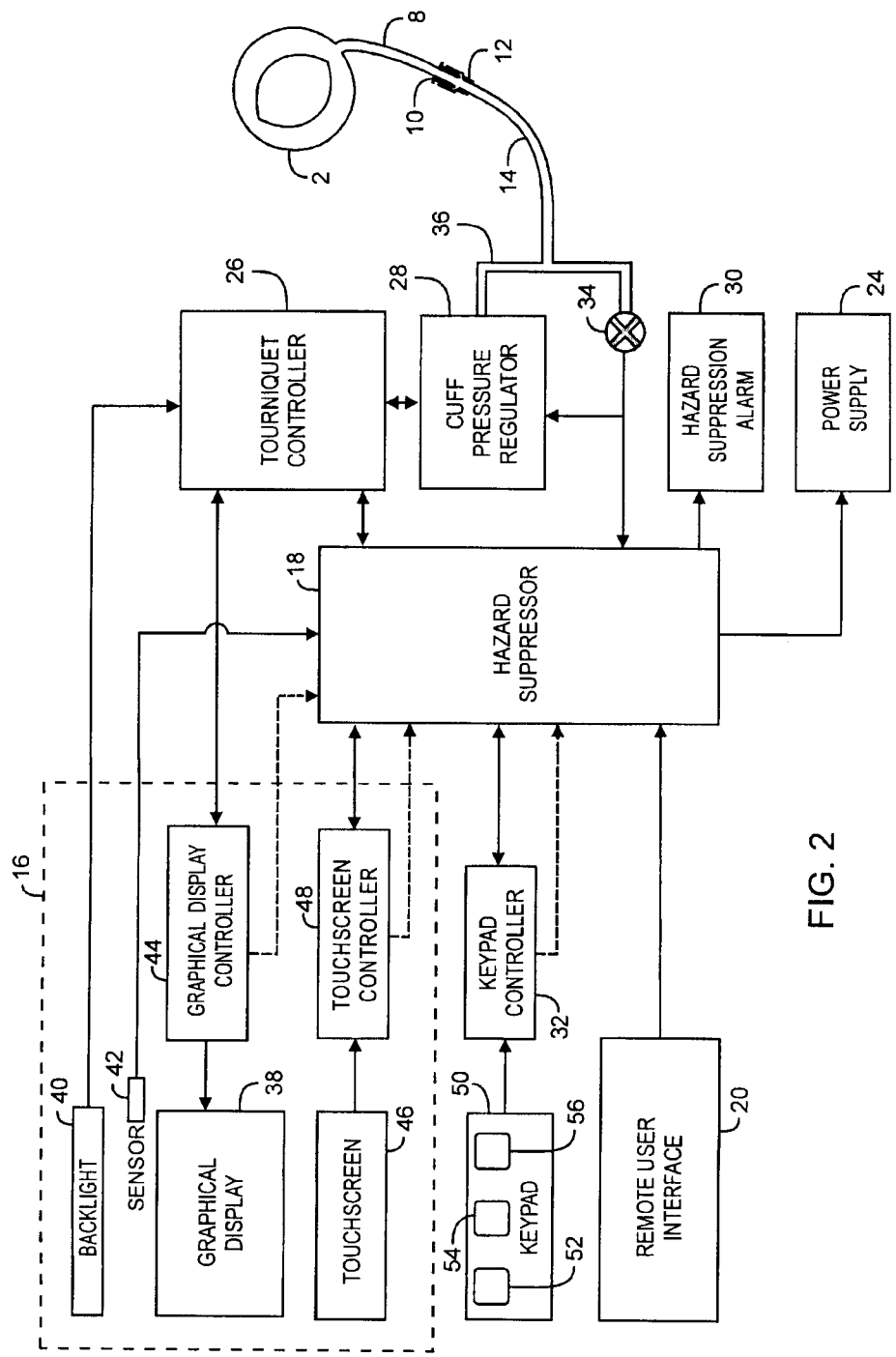
FIG. 2 is block diagram of the preferred embodiment.
Figure 3:
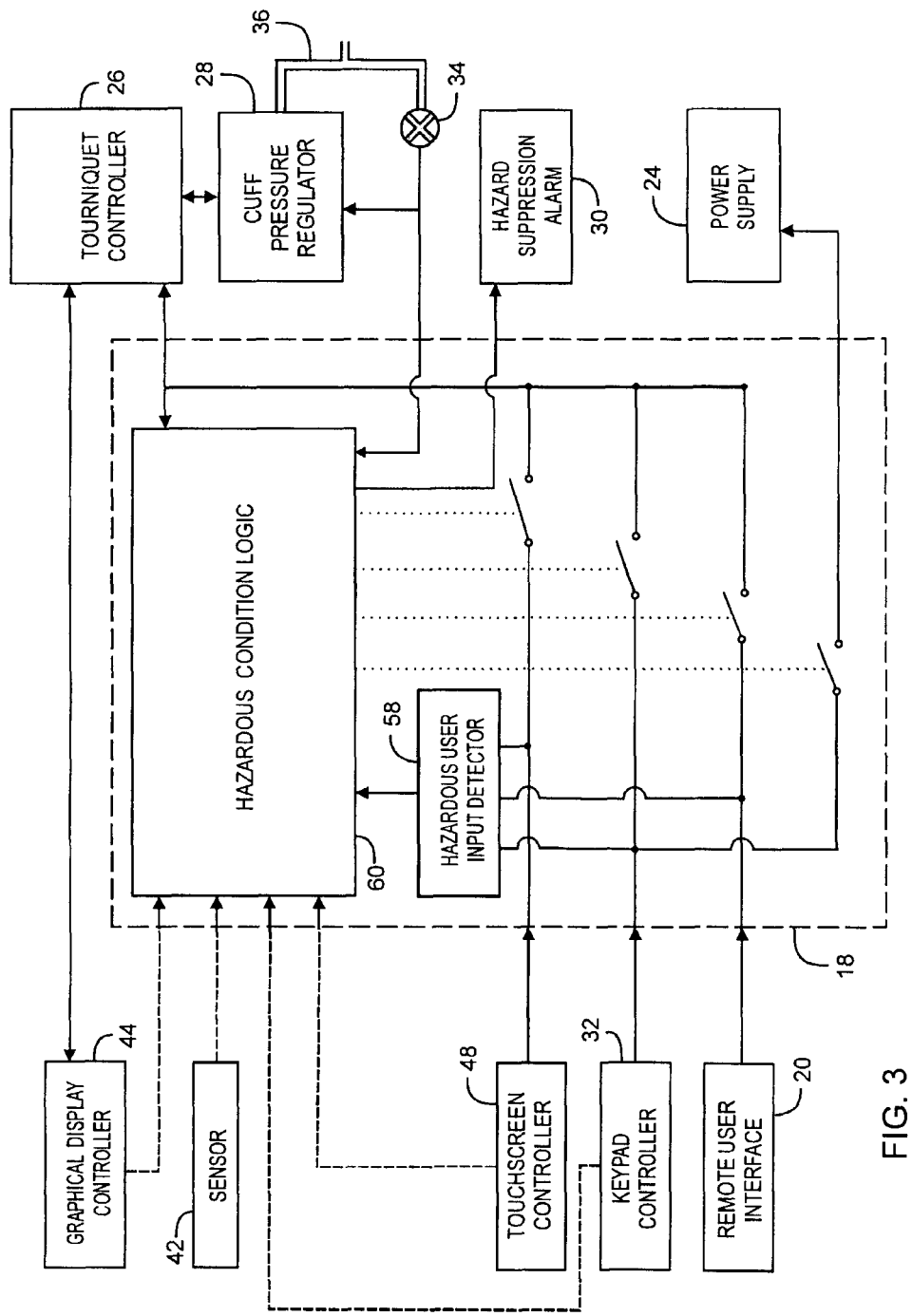
FIG. 3 is an operational schematic of the hazard suppressor of the preferred embodiment.

Remote user interface 20 shown in FIGS. 1 and 2 provides a means for a user to control the operation of instrument 6 at a location remote from instrument 6. Remote user interface 20 includes a touchscreen and operates similar to touchscreen user interface 16. Cable 22 connects remote user interface 20 to instrument 6; alternatively remote user interface 20 and instrument 6 may communicate wirelessly. To provide improved patient safety some user actions are prevented from being initiated from remote user interface 20 under normal circumstances, for example the deflation of cuff 2. In the event of a malfunction of touchscreen user interface 16, actions that are normally prevented from being initiated at remote user interface 20 may be permitted, as described below.

FIG. 2 is a block diagram depicting components of the preferred embodiment. Referring to FIG. 2, power supply 24 supplies electrical power required for the operation of components of instrument 6 including: touchscreen user interface 16, tourniquet controller 26, cuff pressure regulator 28, hazard suppressor 18, hazard suppression alarm 30, keypad controller 32 and pressure transducer 34. In response to a power control signal received from hazard suppressor 18 power supply 24 selectively supplies or interrupts the supply of electrical power to one or more components of instrument 6.

Tourniquet controller 26 is a microcontroller typical of those known in the art with associated program and data memory, analog and digital peripheral interface circuitry, and other support components. Tourniquet controller 26 executes software programs that control the operation of instrument 6. For clarity, and to enable a better understanding of the principles of the invention some functions that may be performed by controller 26 are described and shown in FIG. 2 as separate functional blocks.

Cuff 2 is pneumatically connected to pressure regulator 28 and pressure transducer 34 via cuff port 8, releasable locking connectors 10 and 12, tubing 14 and manifold 36. Pressure transducer 34 produces a cuff pressure signal that is indicative of the pressure of gas within the inflatable portion of cuff 2. The cuff pressure signal is communicated to pressure regulator 28 and hazard suppressor 18.

When supplied with electrical power from power supply 24, pressure regulator 28 can be directed by tourniquet controller 26 to maintain the pressure of gas within cuff 2 (cuff pressure) near a reference pressure level that is communicated to it by tourniquet controller 26. Pressure regulator 28 can also be directed by tourniquet controller 26 to depressurize cuff 2 to a pressure level near zero.

The electrical and pneumatic components of pressure regulator 28 are configured such that, when pressure regulator 28 is not supplied with electrical power from power supply 24, pressure regulator 28 does not permit any escape of gas from cuff 2 or provide any additional gas to cuff 2. Some tourniquet systems of the prior art act to depressurize an attached cuff when the power supply to components of the regulator is interrupted; this is unsafe because if power is removed from a regulator component at a time when surgery is in progress then unexpected blood flow may occur.

Touchscreen user interface 16 is comprised of graphical display 38, backlight 40, light sensor 42, graphical controller 44, touchscreen 46 and touchscreen controller 48. Graphical display 38 is a color TFT LCD display panel with an LED or CCFL backlight. The backlight of graphical display 38 is identified in FIG. 2 as backlight 40. Light sensor 42 produces a signal indicative of the amount of light produced by graphical display 38 which is communicated to hazard suppressor 18. In the preferred embodiment light sensor 42 is a light sensitive sensor such as a photodiode or phototransistor positioned in close proximity to backlight 40. Alternatively, light sensor 42 may comprise part of the circuitry used to supply power to backlight 40, allowing indirect determination of the amount of light produced by graphical display 38. Graphical display 38 may not require a backlight to display information that is visible to a user, by employing other technology such as OLED or plasma; light sensor 42 would then be adapted to directly or indirectly determine the amount of light produced by graphical display 38. The complete failure of backlight 40 makes any information displayed on graphical display 38 invisible to a user, and this is hazardous. A partial failure or reduction in the brightness of backlight 40 may make some information difficult to visually discern by the user in normal ambient lighting conditions, also presenting a hazard.

Touchscreen 46 covers the display surface of graphical display 38. Touchscreen controller 48 determines the presence and location of a user's touch on touchscreen 46. In the preferred embodiment touchscreen 46 and touchscreen controller 48 employ the principle of projected capacitance to determine the presence and location of a user's touch and are capable of determining the presence and location of multiple simultaneous touches by a user. Alternatively a touchscreen employing other principles known in the art to discern the presence and location of a user's touch may be used, for example resistive, surface acoustic wave, and optical principles. Touchscreen controller 48 detects partial or complete malfunctions of its operation and malfunctions in the interface with touchscreen 46 as described below. When touchscreen controller 48 detects a malfunction it communicates a malfunction signal indicative of the detected malfunction to hazard suppressor 18. For example, touchscreen controller 48 may detect one or more broken electrical connections with touchscreen 46 and communicate a malfunction signal to hazard suppressor 18 indicative of a region of touchscreen 46 in which a user's touch cannot be detected.

Graphical controller 44 receives input from tourniquet controller 26 and operates to display images, icons, and text on graphical display 38. When graphical controller 44 detects an error in its operation that may result in incorrect or incomplete information being displayed on graphical display 38, it produces a malfunction signal that is communicated to hazard suppressor 18.

A user of touchscreen interface 16 controls the operation of instrument 6 by touching the touchscreen in an area within the perimeter of a touchscreen key. In the preferred embodiment touchscreen keys are icons and text shown on graphical display 38 that represent an action to be performed when the key is touched by a user. Each touchscreen key has a predetermined area and a predetermined perimeter and is shown at a selected location on graphical display 38. To initiate an action the user touches the touchscreen within the perimeter of the displayed icon or text. As is typical in the art, touchscreen 46 is constructed independently of underlying graphical display 38 and consequently touchscreen 46 indicates the presence and location of a user's touch within the perimeter of a displayed icon or text; at times when the icon or text may not be visible to the user due to a malfunction of the graphical controller 44 or backlight 40, a hazard exists.

Keypad 50 comprises individual input keys 52, 54, and 56. Keypad controller 32 interfaces with keypad 50 and produces signals indicative of the keys touched by a user. Keypad 50 and keypad controller 32 operate independently of touchscreen user interface 16 and keypad 50 is located away from touchscreen user interface 16. In the preferred embodiment, keypad 50 and keypad controller 32 employ the principle of projected capacitance to detect key presses by a user. It will be apparent that alternatively other principles could be used to detect key presses by a user. Key 52 is a power control key and provides a means for a user to interrupt power to selected components of instrument 6. In the preferred embodiment keys 54 and 56 provide a means for the user to enable or disable remote interface 20. Alternatively these discrete keys 52, 54 and 56 could be used to control other actions of instrument 6.

When keypad controller 32 detects an error in its operation or a failure to communicate with keypad 50, it produces a malfunction signal that is communicated to hazard suppressor 18.

An operational schematic of hazard suppressor 18 is shown in FIG. 3. Actions initiated by a user operating touchscreen user interface 16, keypad 50 and remote user interface 20 are communicated from touchscreen controller 48, keypad controller 32 and remote user interface 20 to tourniquet controller 26 through hazard suppressor 18. Keypad controller 32 also communicates with power supply 24 through hazard suppressor 18. Hazard suppressor 18 receives malfunction signals from light sensor 42, graphic controller 44, touchscreen controller 48 and keypad controller 32. Hazard suppressor 18 receives a cuff pressure signal indicative of the pressure in cuff 2 from pressure transducer 34. Hazard suppressor 18 monitors user-initiated actions input via touchscreen user interface 16, keypad 50 and remote user interface 20 to detect potentially hazardous user-initiated actions. In particular, hazard suppressor 18 includes logic 60 that uses the received levels of the malfunction signals and any detected hazardous user-initiated input action (58) to determine a hazard condition and, dependent upon the hazard condition and upon the difference between the actual cuff pressure and reference pressure level, selects which user-initiated action(s) to suppress, which to permit, and whether a confirming action may be required from the user before the desired action is communicated to tourniquet controller 26. When a malfunction or potentially hazardous user-initiated action is detected, hazard suppressor 18 produces a hazard suppression signal that is communicated to tourniquet controller 26 and also activates hazard suppression alarm 30 to alert the user that the desired action has been suppressed.

For example, if hazard suppressor 18 receives a signal from light sensor 42 indicating that icons and text shown on graphical display 38 may not be visible to the user, then hazard suppressor 18 suppresses communication of user-initiated actions via touchscreen user interface 16 to tourniquet controller 26; a user-initiated action at a time when the graphical display 38 may not be producing visible information may result in undesired and hazardous changes in cuff pressure. If the cuff pressure level is near zero when this hazardous condition is detected, hazard suppressor 18 further suppresses communication from remote user interface 20; this prevents user-initiated actions that would pressurize cuff 2 from being communicated to tourniquet controller 26.

If hazard suppressor 18 receives a signal from light sensor 42 indicating that icons and text shown on graphical display 38 are not fully visible to a user (a partial failure of backlight 40), hazard suppressor 18 suppresses the communication of some user-initiated actions via touchscreen interface 16 to tourniquet controller 26: for example, if the cuff pressure level is near the reference pressure level, user-initiated actions that would change the reference pressure level are suppressed.

As shown in FIG. 3, hazard suppressor 18 monitors touchscreen controller 48 for user-initiated actions that are input via touchscreen user interface 16 (FIG. 2), keypad controller 32 and remote user interface 20. This facilitates detection of potentially hazardous user actions (58). If such a detected potentially hazardous action would result in a change in cuff pressure or de-activation of an alarm, the user-requested action is suppressed by hazard suppressor 18.

Touchscreen 46 and touchscreen controller 48 can detect the simultaneous presence of a user's touch at more than one location. When initiating some user actions via touchscreen user interface 16, a user may inadvertently touch more than one location simultaneously or may be required to touch more than one location simultaneously. The partial failure of touchscreen 46 or touchscreen controller 48 may result in false touches being reported by touchscreen controller 48. If hazard suppressor 18 detects that a user has initiated an action by touching touchscreen 46 within the perimeter of a selected touchscreen key and a user's touch is also detected by touchscreen 46 at a location outside the perimeter of the selected touchscreen key, hazard suppressor 18 suppresses communication from touchscreen controller 48 to tourniquet controller 26 and the desired action initiated by the user is not communicated to tourniquet controller 26; additionally a hazard suppression signal is produced and hazard suppression alarm 30 is activated to alert the user that the desired action has been suppressed. Communication from touchscreen controller 48 remains suppressed and the hazard suppression signal remains active until touchscreen 46 no longer senses a user's touch at any location. User-initiated actions that are suppressed by hazard suppressor 18 are dependent upon the nature of the action being initiated by the user and the cuff pressure level.

To assure that a user intends to initiate certain potentially hazardous actions, such as the deflation of cuff 2, the preferred embodiment may require the user to touch two touchscreen keys at the same time. Also, if hazard suppressor 18 detects that the user has also touched the touchscreen at a location outside the perimeters of the two selected touchscreen keys and cuff 2 is pressurized, then hazard suppressor 18 suppresses communication from touchscreen controller 48 to tourniquet controller 26 and the desired action initiated by the user is not communicated to tourniquet controller 26; also a hazard suppression signal and hazard suppression alarm are produced to alert the user that the desired action has been suppressed. Communication from touchscreen controller 48 remains suppressed and the hazard suppression signal remains active until touchscreen 46 no longer senses a user's touch at any location (hence, there is no user input to communicate to the tourniquet controller).

As described above, the preferred embodiment includes a power control key 52. Power control key 52 is interfaced with keypad controller 32 to produce a power control signal when key 52 is actuated; the power control signal is communicated through hazard suppressor 18 to power supply 24 and provides a means for a user to selectively interrupt power to components of instrument 6. Hazard suppressor 18 prevents communication of the power control signal from keypad controller 32 to power supply 24 at times when it would be unsafe to interrupt power to components of the preferred embodiment and also provides a means to override the suppression of the power control signal. For example, if a malfunction of touchscreen user interface 16 is detected by hazard suppressor 18 at a time when the pressure in cuff 2 is near the reference pressure level, indicating that cuff pressure regulator 28 is operating to maintain the pressure in cuff 2 near the reference pressure level, hazard suppressor 18 suppresses communication of the power control signal, thereby preventing power supply 24 from interrupting the supply of power to pressure regulator 28, suppresses communication from touchscreen user interface 16, and activates hazard suppression alarm 30. To enable the user to interrupt power to components of the preferred embodiment at a time when a malfunction is detected, hazard suppressor 18 monitors the power control signal from keypad controller 32 during the time that the malfunction is detected and communicates the power control signal to power supply 24 only if certain override conditions are met: in the preferred embodiment the override conditions are the continued activation of power key 52 by the user for longer than a predetermined time interval of 10 seconds, or the activation of power key 52 by the user at a first time and repeated actuation of power key 52 within a predetermined time interval of 5 seconds. It will be appreciated that other time intervals and sequences may be used by hazard suppressor 18 in determining when to override the power control signal.

As described above a user may set the level of pressure to be maintained in cuff 2 (reference pressure level) both via touchscreen user interface 16 and via remote user interface 20. To prevent inadvertent or unintended changes to the reference pressure level by the user, hazard suppressor 18 detects user-initiated actions input via touchscreen user interface 16 and remote user interface 20 that set the level of the reference pressure. If a user action would set the reference pressure level to a level that is significantly different from the cuff pressure sensed by pressure transducer 34, the action is suppressed and the hazard suppression alarm is activated. In the preferred embodiment a significant difference between the cuff pressure and a desired reference pressure level is 50 mmHg for reference pressure levels set via touchscreen user interface 16 and 25 mmHg for reference pressure levels set via remote user interface 20. For example, if the pressure in cuff 2 is 250 mmHg and a user-initiated action to set the reference pressure level to 400 mmHg via touchscreen user interface 16 is detected by hazard suppressor 18, the desired reference pressure setting is suppressed; if the pressure in cuff 2 is 250 mmHg and a user-initiated action to set the reference pressure level to 300 mmHg via touchscreen user interface 16 is detected then the user-initiated action to set the reference pressure level to 300 mmHg is communicated to tourniquet controller 26. It will be apparent that other values for a significant pressure difference between cuff pressure and desired reference pressure level may be used by hazard suppressor 18. Moreover, the suppression may, in some instances, be overridden by a user's response to confirming input requested by the hazard suppressor 18.

Other equipment and user interfaces may communicate with tourniquet controller 26 through hazard suppressor 18. For example, tourniquet controller 26 may be configured to adapt the cuff reference pressure level in response to changes in a physiologic parameter of the patient, in a manner similar to that described in U.S. Pat. App. Pub. No. 20080262533, herein incorporated by reference, but with certain hazards suppressed: for example, a remote physiologic monitor for monitoring changes in a physiologic parameter of a patient may communicate with tourniquet controller 26 through hazard suppressor 18 so that, at times when a malfunction or input error is detected, communication is suppressed and tourniquet controller 26 is prevented from responding to monitored physiologic changes.

We claim:

1. A surgical tourniquet system having a hazard suppressor, comprising:
    a touchscreen user interface including a graphical display adapted for displaying information visually to a user, wherein the graphical display is further adapted to show a touchscreen key corresponding to a desired action of a tourniquet controller, and wherein the touchscreen user interface detects actuation of the touchscreen key by the user and produces a user input signal upon actuation;
    a tourniquet controller communicating with the touchscreen user interface through a hazard suppressor and further communicating with a cuff pressure regulator, wherein the cuff pressure regulator is connected pneumatically to a tourniquet cuff applied to a surgical patient;
    a cuff pressure transducer for sensing a level of pressure in the tourniquet cuff and for producing a cuff pressure signal indicative of the level of pressure sensed; and
    the hazard suppressor adapted for detecting a malfunction of the touchscreen user interface and responsive to the cuff pressure signal, wherein the hazard suppressor suppresses communication of the user input signal to the tourniquet controller if the malfunction is detected at a time when the level of pressure indicated by the cuff pressure signal differs substantially from a reference level.

2. The apparatus of claim 1 wherein the reference level is zero and wherein the desired action is depressurization of the tourniquet cuff.

3. The apparatus of claim 1 wherein the hazard suppressor is located remotely from the touchscreen user interface.

4. The apparatus of claim 3 wherein the touchscreen user interface communicates by wireless means with the tourniquet controller through the hazard suppressor.

5. The apparatus of claim 1 wherein the cuff pressure regulator is normally operable for maintaining tourniquet cuff pressure near the reference level during a time period of a surgical procedure,
    and including a remote apparatus operable independently of the touchscreen user interface for producing a remote input signal indicative of a second reference level, wherein the remote apparatus communicates the remote input signal to the tourniquet controller through the hazard suppressor, and wherein the hazard suppressor further suppresses communication of the remote input signal to the tourniquet controller if the difference between the reference level and the second reference level is greater than a predetermined difference.

6. The apparatus of claim 1 and including a power supply for supplying electrical power to the touchscreen user interface, the hazard suppressor, the tourniquet controller and the cuff pressure regulator, and wherein the desired action is interruption of supply of electrical power.

7. The apparatus of claim 1 wherein the hazard suppressor further produces a hazard suppression signal when communication is suppressed, and including a hazard suppression alarm operable independently of the touchscreen user interface to produce a hazard suppression alarm perceptible to the user in response to the production of hazard suppression signal.

8. The apparatus of claim 1 wherein the hazard suppressor further produces a hazard signal when the malfunction is detected.

9. The apparatus of claim 1, wherein the touchscreen user interface includes a light sensor for sensing a level of light produced by the graphical display of the touchscreen user interface and for producing a light level signal indicative of the level of light sensed, and wherein the hazard suppressor detects the malfunction when the level of light indicated by the light level signal is less than a predetermined minimum light threshold.

10. The apparatus of claim 9 wherein the hazard suppressor further produces a display hazard alarm if the level of light indicated by the light level signal is greater than the predetermined minimum light threshold and less than a low-light threshold, wherein the low-light threshold is greater than the predetermined minimum light threshold.

11. The apparatus of claim 1 wherein the graphical display of the touchscreen user interface communicates with the tourniquet controller through a graphical display controller, wherein the graphical display controller produces a display controller malfunction signal indicative of a malfunction of the graphical display controller, and wherein the hazard suppressor detects the malfunction of the touchscreen user interface in response to the production of the display controller malfunction signal.

12. The apparatus of claim 1 wherein the touchscreen key displays an icon representing the desired action of the tourniquet controller.

13. A surgical tourniquet system having a hazard suppressor, comprising:
a touchscreen user interface for displaying information visually to a user and including a touchscreen key adapted for actuation by the user to produce a user input signal;
a tourniquet controller communicating with the touchscreen user interface through a hazard suppressor and further communicating with a cuff pressure regulator, wherein the cuff pressure regulator is connected pneumatically to a tourniquet cuff applied to a surgical patient;
a power supply responsive to a power control signal for selectively supplying and interrupting electrical power to each of the touchscreen user interface, the tourniquet controller, the cuff pressure regulator, a hazard suppression alarm and the hazard suppressor, each requiring supply of electrical power for operation;
the hazard suppression alarm responsive to a hazard suppression signal and operable independently of the touchscreen user interface for producing a hazard suppression alarm perceptible to the user if the hazard suppression signal is produced;
a power control key operable independently of operation of the touchscreen user interface and located away from the touchscreen user interface, wherein the power control key detects an actuation by the user and produces the power control signal indicative of the actuation; and
the hazard suppressor adapted for detecting a malfunction of the touchscreen user interface and responsive to the power control signal, wherein the hazard suppressor suppresses communication of the power control signal to the power supply when the malfunction is detected, and wherein the hazard suppressor further produces the hazard suppression signal when communication is suppressed.

14. The apparatus of claim 13 wherein the hazard suppressor includes override means operable if the power control signal indicates actuation of the power control key for a time period greater than a predetermined maximum normal actuation time after the malfunction is detected, wherein the override means is operable for communicating the power control signal to the power supply while the malfunction is detected.

15. The apparatus of claim 13 wherein the hazard suppressor includes override means operable if the power control signal indicates actuation of the power control key for a time period greater than a predetermined maximum normal actuation time after the malfunction is detected, wherein the override means is operable for inhibiting production of the hazard suppression signal.

16. The apparatus of claim 13 wherein the hazard suppressor includes override means operable when the malfunction is detected and if the power control signal indicates a first actuation of the power control key by the user and a second confirming actuation within a predetermined override period after the first actuation, and wherein the override means is operable by communicating the power control signal to the power supply after the malfunction is detected.

17. The apparatus of claim 16 wherein the actuation by the user initiates an interruption of supply of electrical power.

18. The apparatus of claim 13 where the power control key communicates with the hazard suppressor through a keypad controller, wherein the hazard suppressor is further adapted for detecting a malfunction of the keypad controller, and wherein the hazard suppressor further suppresses communication of the power control signal to the power supply when the malfunction of the keypad controller is detected.

19. A surgical tourniquet system having a hazard suppressor, comprising:
a touchscreen user interface including a graphical display adapted for displaying information visually to a user, wherein the graphical display is further adapted to show a touchscreen key corresponding to a desired action of a tourniquet controller, and wherein the touchscreen user interface detects actuation of the touchscreen key by the user and produces a user input signal upon actuation;
a tourniquet controller communicating with the touchscreen user interface through the hazard suppressor and further communicating with a cuff pressure regulator, wherein the cuff pressure regulator is connected pneumatically to a tourniquet cuff applied to a surgical patient; a cuff pressure transducer for sensing a level of pressure in the tourniquet cuff and for producing a cuff pressure signal indicative of the level of pressure sensed;

a power supply responsive to a power control signal produced by a power control key for selectively supplying and interrupting electrical power to at least the touchscreen user interface, the tourniquet controller, the cuff pressure regulator, the cuff pressure transducer, a hazard suppression alarm and the hazard suppressor, each requiring supply of electrical power for operation;

a power control key detecting an actuation by the user and for producing the power control signal indicative of the actuation; and the hazard suppressor operable by detecting a malfunction of the touchscreen user interface at a detection time when the level of pressure indicated by the cuff pressure signal is substantially greater than zero, and further operable upon detection of the malfunction at the detection time by suppressing communication of the user input signal to the tourniquet controller, suppressing communication of the power control signal to the power supply; and wherein the hazard suppressor includes override means enabling the user to override only suppression of communication of the power control signal to the power supply after detection of the malfunction at the detection time.

20. The apparatus of claim 19 wherein the hazard suppressor further produces a hazard suppression signal upon detection of the malfunction at the detection time and including a hazard suppression alarm responsive to the hazard suppression signal and operable independently of the touchscreen user interface for producing a hazard suppression alarm perceptible to the user.

21. The apparatus of claim 19 and wherein detection of actuation of the power control key is independent of operation of the touchscreen user interface and wherein the power control key is located away from the touchscreen user interface.

22. The apparatus of claim 21 wherein the override means overrides suppression of communication of the power control signal to the power supply if the power control signal indicates actuation of the power control key by the user for a time period greater than a predetermined maximum normal actuation time.

23. The apparatus of claim 21 wherein the override means overrides suppression of communication of the power control signal to the power supply if the power control signal indicates a first actuation of the power control key by the user after detection of the malfunction at the detection time and a second confirming actuation by the user within a predetermined override period after the first actuation.

24. A surgical tourniquet system having a hazard suppressor, comprising:

a touchscreen user interface including a graphical display adapted for displaying information visually to a user, wherein the graphical display is further adapted to show a touchscreen key, wherein the touchscreen key is shown as an icon representing a desired action of a tourniquet controller within a predetermined touchscreen key perimeter defining a predetermined touchscreen key area at a selected position on the graphical display, and wherein the touchscreen user interface is operable for detecting actuation by sensing a presence of a touch of the user on a region of the graphical display, and wherein the touchscreen user interface is further operable for producing a user input signal indicative of the presence and the region of the touch;

a tourniquet controller communicating with the touchscreen user interface through the hazard suppressor and further communicating with a cuff pressure regulator, wherein the cuff pressure regulator is connected pneumatically to a tourniquet cuff applied to a surgical patient;

a cuff pressure transducer for sensing a level of pressure in the tourniquet cuff and for producing a cuff pressure signal indicative of the level of pressure sensed; and the hazard suppressor responsive to the user input signal indicative of the presence and region of the touch and adapted for producing a user hazard suppression signal if at least a portion of the region of the touch is located outside the predetermined touchscreen key perimeter, and wherein the hazard suppressor is further adapted for suppressing communication of the user input signal to the tourniquet controller if the user hazard suppression signal is produced at a time when the level of pressure indicated by the cuff pressure signal differs substantially from a reference level.

25. The apparatus of claim 24 wherein the reference level is zero and wherein the desired action is depressurization of the tourniquet cuff.

26. The apparatus of claim 24 wherein the cuff pressure regulator is normally operable for maintaining tourniquet cuff pressure near the reference level during a time period of a surgical procedure, and including a remote apparatus operable independently of the touchscreen user interface for producing a remote input signal indicative of a remote reference value, wherein the remote apparatus communicates the remote input signal to the tourniquet controller through the hazard suppressor, wherein the tourniquet controller includes means for changing the reference level to the remote reference value in response to the remote input signal, and wherein the hazard suppressor further suppresses communication of the remote input signal to the tourniquet controller if a difference between the reference level and the remote reference value is greater than a predetermined difference.

27. The apparatus of claim 24 wherein the graphical display is further adapted to show a second touchscreen key, wherein the second touchscreen key is a second icon representative of a second action of the tourniquet controller within a second predetermined touchscreen key perimeter defining a second predetermined touchscreen key area at a second selected position on the graphical display, and wherein the touchscreen user interface is further operable for sensing a presence of a second touch of the user on a second region of the graphical display, and wherein the touchscreen user interface is further operable for producing a second user input signal indicative of the presence and the region of the second touch; and wherein the hazard suppressor is further adapted for producing a user hazard suppression signal if at least a portion of the region of the second touch is located outside the second predetermined touchscreen key perimeter, and wherein the hazard suppressor is further adapted for suppressing communication of the second user input signal to the tourniquet controller if the user hazard suppression signal is produced at a time when the level of pressure indicated by the cuff pressure signal differs substantially from the reference level.

28. The apparatus of claim 24 and including a hazard suppression alarm responsive to production of the user hazard suppression signal, wherein the hazard suppression alarm is perceptible to the user and operable independently of the of operation of the touchscreen user interface.

29. The apparatus of claim 24, wherein the user hazard suppressor further stops production of the hazard suppression signal upon detecting an interruption of the presence of the touch.

30. A surgical tourniquet system having a hazard suppressor, comprising:
   a touchscreen user interface including a graphical display adapted for displaying information visually to a user wherein the graphical display is further adapted to show first and second touchscreen keys,
   wherein the first touchscreen key is shown as a first icon within a predetermined touchscreen key perimeter defining a predetermined touchscreen key area at a selected position on the graphical display,
   wherein the second touchscreen key is shown as a second icon within a second predetermined touchscreen key perimeter defining a second predetermined touchscreen key area at a second selected position on the graphical display, and
   wherein the touchscreen user interface is operable for detecting actuation by sensing a presence of a touch of the user on a plurality of regions of the graphical display, and wherein the touchscreen user interface is further operable for producing a user input signal indicative of the presence and the plurality of regions of the touch;
   a tourniquet controller communicating with the touchscreen user interface through the hazard suppressor and further communicating with a cuff pressure regulator, wherein the cuff pressure regulator is connected pneumatically to a tourniquet cuff applied to a surgical patient;
   a cuff pressure transducer for sensing a level of pressure in the tourniquet cuff and for producing a cuff pressure signal indicative of the level of pressure sensed; and
   the hazard suppressor adapted for communicating the user input signal to the tourniquet controller if the presence of the touch is sensed entirely within the first and second touchscreen key perimeters simultaneously at a time when the level of pressure indicated by the cuff pressure signal differs substantially from zero, wherein the hazard suppressor is further adapted for suppressing communication of the user input signal to the tourniquet controller and for producing a user hazard suppression signal if a region of the touch is sensed outside the first and second touchscreen key perimeters at the time.

31. The apparatus of claim 30 wherein the first and second icons represent one action of the tourniquet controller desired by the user.

32. The apparatus of claim 30 wherein the first and second icons represent an action of the tourniquet controller depressurizing the tourniquet cuff.

33. The apparatus of claim 30 wherein the first icon represents a first action of the tourniquet controller desired by the user and wherein the second icon represents a second action.

34. The apparatus of claim 33 wherein the tourniquet controller is powered electrically to regulate pressure in the tourniquet cuff near a reference pressure level, wherein the first action represents an interruption of electrical power to the tourniquet controller, and wherein the and the second action represents confirmation of the first action by the user.

* * * * *